(12) United States Patent
Schena et al.

(10) Patent No.: US 7,842,018 B2
(45) Date of Patent: Nov. 30, 2010

(54) COLOSTOMY BAG CLEANING SYSTEM

(76) Inventors: Blaine M. Schena, 1717 Camelia La., Naples, FL (US) 34105; Kenneth R. Schena, 2313 Harrier Run, Naples, FL (US) 34105

(*) Notice: Subject to any disclaimer, the term of this patent is extended or adjusted under 35 U.S.C. 154(b) by 0 days.

(21) Appl. No.: 10/874,294

(22) Filed: Jun. 21, 2004

(65) Prior Publication Data

US 2005/0283126 A1    Dec. 22, 2005

(51) Int. Cl.
*A61F 5/442*    (2006.01)
*A61F 5/448*    (2006.01)
*A61F 5/449*    (2006.01)

(52) U.S. Cl. .................... 604/344; 604/334; 604/342

(58) Field of Classification Search ............... 604/317, 604/327, 332–345
See application file for complete search history.

(56) References Cited

U.S. PATENT DOCUMENTS

| | | | | |
|---|---|---|---|---|
| 1,121,667 A * | 12/1914 | Ross | ............. | 604/297 |
| 1,388,621 A * | 8/1921 | Umbsen | ............. | 604/297 |
| 1,398,208 A * | 11/1921 | Trial | ............. | 4/617 |
| 1,577,345 A * | 3/1926 | Nagorski et al. | ............. | 4/618 |
| 2,025,492 A * | 12/1935 | Aird | ............. | 604/334 |
| 2,330,695 A * | 9/1943 | Eweson | ............. | 604/301 |
| 2,438,073 A * | 3/1948 | Saur | ............. | 604/277 |
| 2,689,567 A * | 9/1954 | Welch | ............. | 604/277 |
| 2,695,024 A * | 11/1954 | Krohmann | ............. | 604/334 |
| 2,782,785 A * | 2/1957 | Arcand | ............. | 604/334 |
| 2,869,547 A * | 1/1959 | Yohe | ............. | 604/334 |
| 4,134,404 A * | 1/1979 | Williams, Jr. | ............. | 604/277 |
| 4,194,506 A | 3/1980 | Voorhies | | |
| 4,265,244 A * | 5/1981 | Hill | ............. | 604/175 |
| 4,413,994 A * | 11/1983 | Sarashina | ............. | 604/327 |
| 4,460,359 A * | 7/1984 | Fenton | ............. | 604/277 |
| 4,592,750 A * | 6/1986 | Kay | ............. | 604/337 |
| 4,596,566 A * | 6/1986 | Kay | ............. | 604/343 |
| 4,654,037 A * | 3/1987 | Fenton | ............. | 604/334 |
| 4,668,227 A * | 5/1987 | Kay | ............. | 604/289 |
| 4,778,446 A * | 10/1988 | Jensen | ............. | 604/27 |

(Continued)

FOREIGN PATENT DOCUMENTS

CA        2130294 A1 *   2/1996

(Continued)

OTHER PUBLICATIONS

Merriam-Webster OnLine definitions of "manifold", "pipe fitting", "spray", "inject" and "jet".*

*Primary Examiner*—Karin M Reichle
(74) *Attorney, Agent, or Firm*—Maier & Maier, PLLC

(57) ABSTRACT

A colostomy bag having a cleansing system wherein the bag is cleaned while in its operable position associated with the person. More specifically, the system mounts a manifold within the colostomy bag with an access to water under pressure from outside, the manifold providing a spray dispersion of fluid, or cleansing water, at the top of the bag and gravity then drips it down through the bag and out the open bottom end, with the residue of the bag being washed out by the water and passing into a toilet. The user can thus easily flush the bag to complete cleaning with all residue from the bag passing into the toilet. A water source from the toilet itself, or other suitable water supply, provides the water under pressure to the manifold inside the top of the colostomy bag.

4 Claims, 4 Drawing Sheets

U.S. PATENT DOCUMENTS

| | | | |
|---|---|---|---|
| 4,810,250 A * | 3/1989 | Ellenberg et al. | 604/277 |
| 4,867,749 A * | 9/1989 | Steer | 604/337 |
| 4,911,699 A * | 3/1990 | Fenton | 604/333 |
| 5,030,214 A * | 7/1991 | Spector | 604/301 |
| 5,096,503 A | 3/1992 | Wellman | |
| 5,125,133 A * | 6/1992 | Morrison | 24/30.5 R |
| 5,454,389 A | 10/1995 | Hubbard et al. | |
| 5,470,325 A * | 11/1995 | Fundock | 604/332 |
| 5,503,633 A * | 4/1996 | Saunders et al. | 604/332 |
| 5,524,357 A * | 6/1996 | Crabb | 34/202 |
| 5,738,668 A | 4/1998 | Bugajski | |
| 5,800,415 A * | 9/1998 | Olsen | 604/336 |
| 6,224,581 B1 | 5/2001 | Withers et al. | |
| 6,408,861 B1 | 6/2002 | Ortega | |
| 6,532,971 B2 * | 3/2003 | Deecki | 134/22.18 |
| 6,918,898 B2 * | 7/2005 | King | 604/334 |
| 7,090,664 B2 * | 8/2006 | Holter | 604/332 |
| 2003/0229324 A1 | 12/2003 | King | |
| 2004/0054339 A1 * | 3/2004 | Ciok et al. | 604/334 |
| 2004/0237969 A1 * | 12/2004 | Fuller | 128/858 |
| 2005/0075616 A1 * | 4/2005 | Holter | 604/332 |
| 2006/0106354 A1 * | 5/2006 | Vantroostenberghe | 604/335 |
| 2006/0253090 A1 * | 11/2006 | Bradley et al. | 604/334 |

FOREIGN PATENT DOCUMENTS

WO    WO 2004/049984 A2 *    6/2004

* cited by examiner

COLOSTOMY BAG CLEANING SYSTEM

BACKGROUND OF THE INVENTION

A colostomy is a surgical procedure in which the colon or a portion thereof is removed and the digestive tract is attached to an opening created in the abdominal wall, thereby, allowing digested waste to pass through the abdomen. Typically, the waste is then collected by an impervious bag that is secured over the opening. The opening that results from a colonectomy is known as an "ostomy" or a "stoma," and the impervious bag that collects the digestive waste is known as a colostomy bag.

An individual who has had a colostomy must typically remove and empty the colostomy bag several times a day, and must irrigate the ostomy at least every other day to maintain good health and sanitation. An ostomy is irrigated by applying flowing water into the ostomy and then allowing the water to drain.

Examples of ostomy irrigating devices in the prior art or cleansing systems are provided by U.S. patent application Publication No. US2003/0229324, which features a closed drainage system that eliminates the necessity to stand over a toilet, as it has its own collection system, but it is a difficult system to use and almost requires the person to be lying down as illustrated in FIG. 1 for any satisfactory use. U.S. Pat. No. 6,408,861 illustrates a urine bag cleaning manifold, which is a very complicated system associated with a shower in a bathtub, and again, is difficult to operate and very elaborate in design. U.S. Pat. No. 5,454,389 teaches an ostomy bag cleaning device that incorporates a mechanism for introducing water into a colostomy bag and then evacuate the waste material into a storage chamber. This device is cumbersome to use and does not provide for a simple cleaning of the colostomy bag without removal from the person.

U.S. Pat. Nos. 5,096,503 and 4,194,506 both teach the general concept of insertion rods being inserted from the bottom of the colostomy bag up into the bag itself, and in both of these systems it's awkward to have to insert a rod up through the bottom of the colostomy bag with whatever drippings and materials that would be coming out, and this is not a satisfactory technique for cleaning the colostomy bag while having the bag still maintained on the person. A similar patent is U.S. Pat. No. 5,738,668, which again inserts a probe up into the bag for cleaning, and again the same problems are inherent. U.S. Pat. No. 6,532,971 teaches a sanitary pouch washer that is designed for simultaneously cleaning the inside and outside of the colostomy bag and is a complicated mechanism and, again, is done with the colostomy bag removed from the person. U.S. Pat. No. 6,224,581 teaches a colostomy bag cleaning appliance having a mounting plate and, again, this is a cleaning method with the bag removed from the person and creates significant complications in achieving the cleaning in a simple and effective manner.

SUMMARY OF THE INVENTION

The present invention is a cleaning system for externally cleaning stomas and cleaning colostomy bags utilizing a manifold physically located near the top of the bag that provides a stream of water in a sprayed fashion for internally cleaning the bag and simultaneously cleaning the exposed surfaces of the stoma, and with the amount of fluid under pressure added being controlled by the user, the bag still being in place or an operable position on the person or wearer, and the flow from the bag coming out the bottom with the normal opening type bags available today.

A colostomy bag is disclosed, which includes a bag having an inlet and an outlet that is repeatedly sealable. A circular manifold can surround the inlet. The manifold can have a plurality of holes arranged in a circumferential relationship on a perimeter of the manifold. The plurality of holes can be sized for spraying fluid. The plurality of holes can number ten or greater. The plurality of holes can be adapted to direct fluid toward the center of the inlet. An access tube can be connected to the manifold for delivering fluid from an outside fluid source for passage through the plurality of holes of the manifold. The colostomy bag can also include a hose having a first end and a second end. The access tube can be attached to the first end of the hose and the second end of the hose can be attached to the outside fluid source. The colostomy bag can further include a first plastic ring having a first flange. The first ring can be attached to the bag where the first ring surrounds the inlet and the manifold. The colostomy bag can be worn in an operable position for collecting digestive waste and the colostomy bag can be irrigated and cleaned while in the operable position.

A colostomy bag irrigation system is also disclosed that can include a bag, a hose and a patch. The colostomy bag can include an inlet and an outlet that is repeatedly sealable. A circular manifold can surround the inlet. The manifold can have a plurality of holes arranged in a circumferential relationship on a perimeter of the manifold. The plurality of holes can be sized for spraying fluid. The plurality of holes can number ten or greater. The plurality of holes can be adapted to direct fluid toward the center of the inlet. The plurality of holes can be adapted to direct fluid toward a stoma of a user when in use. An access tube can be connected to the manifold for delivering fluid from an outside fluid source for passage through the plurality of holes of the manifold. The hose can be adapted to bridge the access tube and the outside fluid source. The colostomy bag can be worn in an operable position for collecting digestive waste and the colostomy bag can be irrigated and cleaned while in the operable position. The patch can have an opening and can be attachable proximate the stoma of a user where the patch is matable with the bag for creating a fluid tight seal. The system can further include a first ring having a first flange. The first ring can be attached to the bag where the first ring surrounds the inlet and the manifold. A second ring having a second flange can be attached to the patch where the first flange is snap-fittingly matable with the second flange for creating a fluid tight seal between the first ring and the second ring.

Accordingly, it is a principal object of the invention to facilitate cleaning of the colostomy bag and simultaneously cleaning the exposed surfaces of the stoma by providing a manifold near the top of the colostomy bag that is connected to a source of water under some pressure that can then controllably sprinkle water into the colostomy bag for cleaning of the bag and the stoma, with the flow then directed out the bottom end of the normal opening-type colostomy bags. The person still has the colostomy bag attached to their body, and the cleaning takes place preferably in association with drainage into a toilet or other suitable drainage facility.

A further object of the invention is to provide that the cleaning of the colostomy bag take place with the bag still attached to the body of the person, and it can be done quickly and very effectively on a regular basis during the day.

It is a further object of the invention to provide the manifold in conjunction with a standard colostomy bag flange, which is a flanged ring with adhesive backing that is typically secured to the abdomen of a person with a stoma. The flange allows a colostomy bag to be easily attached and detached. The colostomy bag attaches to the flanged ring much like a TUPPER- WARE lid attaches to a TUPPERWARE bowl, i.e., the colostomy bag and flange snap together to form an airtight seal. Consequently, a cleaning system that uses the same flanged ring is also easily attached and detached and, further, does not necessitate the removal of the bag from the person for the cleaning.

Finally, it is an object of the invention to provide improved elements and arrangements thereof for the purposes described, which is inexpensive, dependable and fully effective in accomplishing its intended purposes.

These and other objects of the present invention will become readily apparent upon further review of the following specifications and drawings.

BRIEF DESCRIPTION OF THE DRAWINGS

Referring now to FIG. 1, of the drawings, the numeral 10 indicates a colostomy bag, which has an inlet opening 12 that is surrounded by a plastic ring 14 and attached in a fluid-tight fashion to the bag 10 by suitable means, such as adhesively or by other suitable known means. The ring 14 is formed with a flange that is designed to mate with a similarly formed ring and flange 14A on the person mounted colostomy bag attachment patch 16. The patch 16 is attached by pressure-sensitive adhesive on the back of the patch itself and the respective ring flanges 14 and 14A when snapped together form a fluid-tight seal between the ostomy 18 and the interior of the colostomy bag 10.

Figure 1:
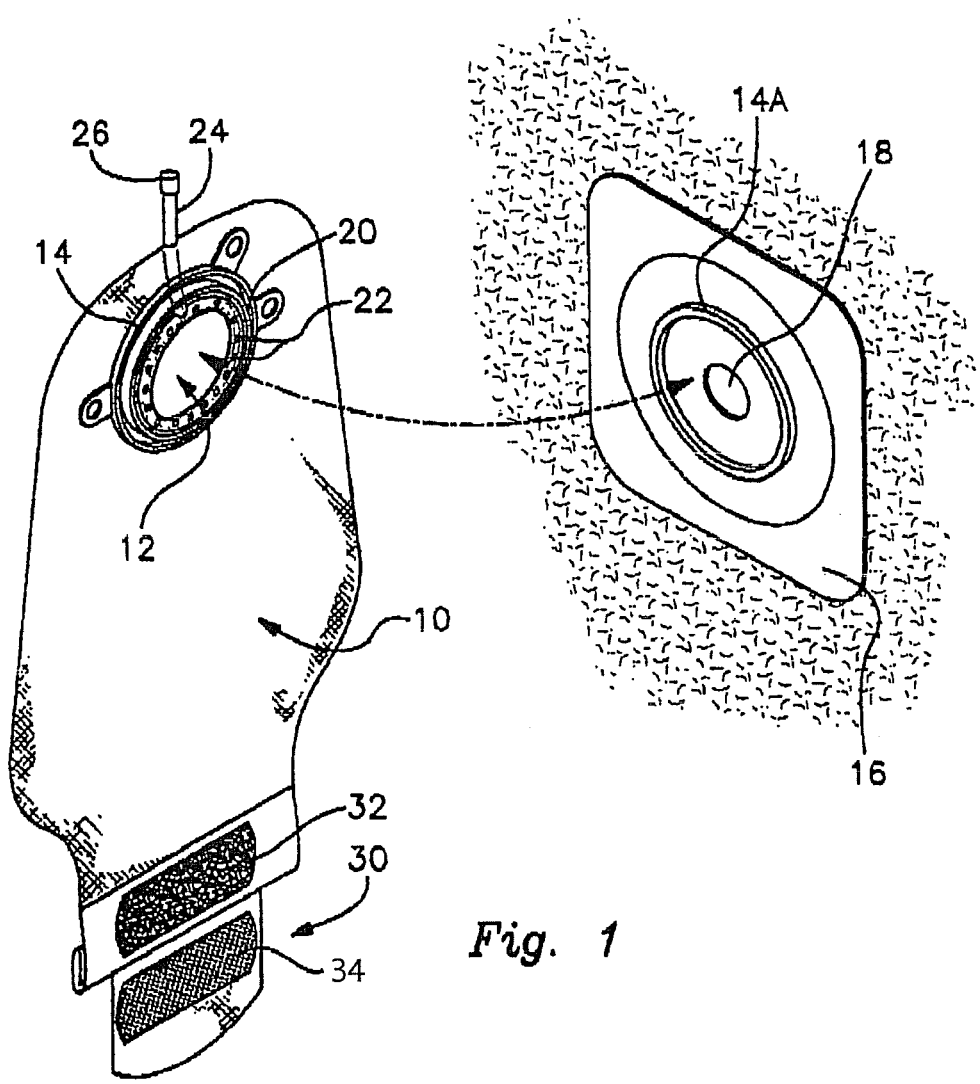
FIG. 1 is a perspective view of the colostomy bag utilizing a manifold around the flanged opening on the bag itself, which then attaches to the flanged fitting or ring positioned on the body of the person, and snaps together to form a fluid-tight seal between the bag and the person.

The irrigating and cleansing technique of the invention is provided by a circular manifold, generally indicated by numeral 20, which is preferably a soft plastic and encircles the interior of the opening 12 into the colostomy bag 10. A plurality of small holes or orifices 22 around the perimeter of the manifold 20 are provided to allow the passage of spray in multiple and random directions of water under pressure introduced through an access tube or conduit or access fitting 24 that is connected to a water source not shown via fitting or adaptor 26.

The colostomy bag 10 in the usual fashion is designed to be opened at the bottom end, generally identified by numeral 30, and effectively, this is a rolled up sealing procedure utilizing hook and loop material indicated by the loop material 32 and the hook material 34. It is well understood that when this is folded up and the hook and loop attachment is in place the bag is sealed at the bottom end, but for the purposes of the irrigation and cleansing of the instant invention, the bag is opened and positioned over the toilet so that irrigation cleansing fluid passing through the manifold 20 and orifices 22 will flow down through the bag and out the bottom end 30 and into the toilet, as is shown in more detail in FIG. 2 of the drawings.

Figure 2:
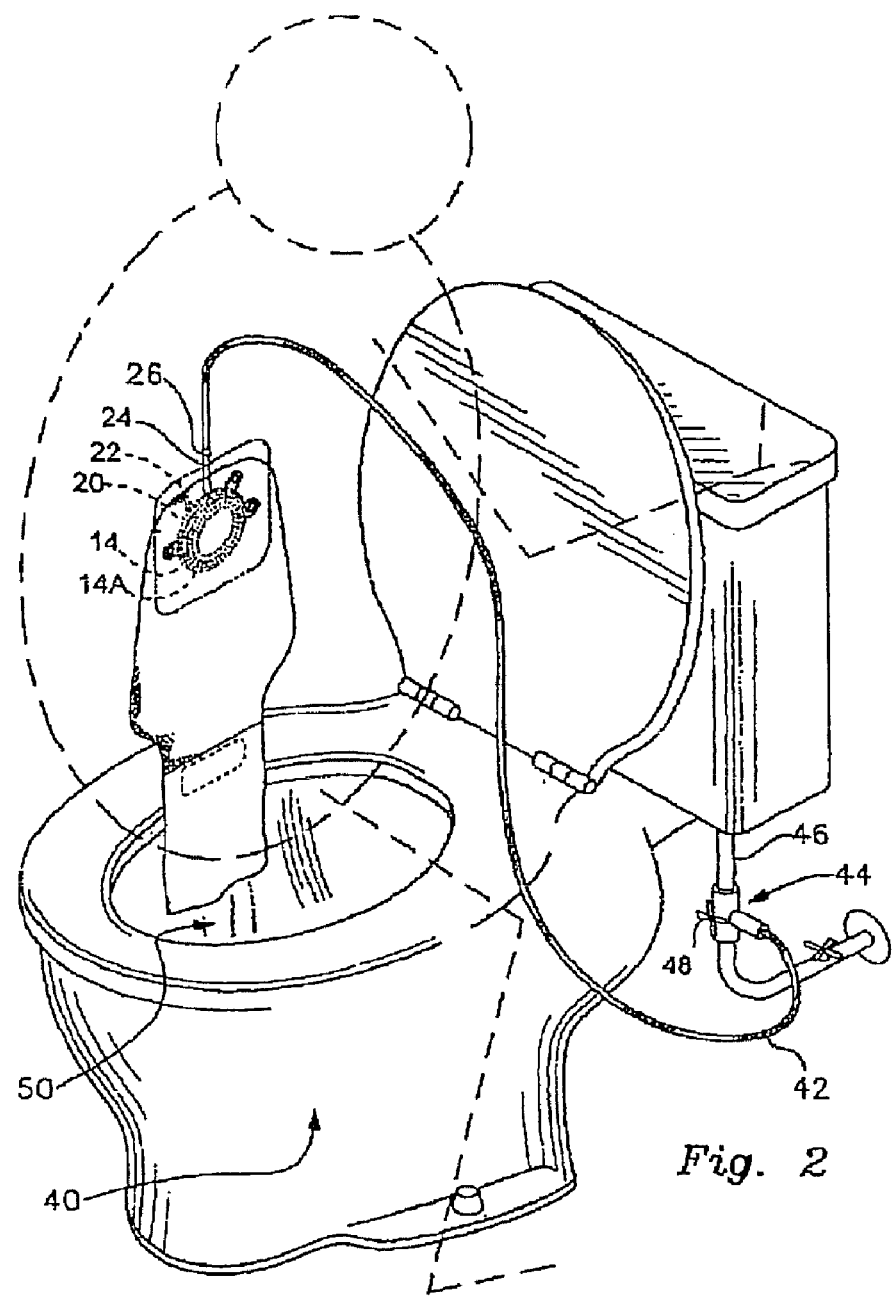
FIG. 2 is a perspective illustration showing a stick figure utilizing the invention by irrigating and flushing the colostomy bag by controlling a valve from the water supply to the toilet with the bottom of the colostomy bag open and flow taking place from the manifold through the bag and into the toilet.

Referring now to FIG. 2, this illustrates a normal toilet indicated generally by numeral 40, and the individual normally sits backward on the toilet seat to operate the invention. A flexible water hose 42 is connected to the fitting 26 to provide water under pressure through the conduit 24 and to the manifold 20 for 7 spray out the orifices 22. The water source is by a fitting indicated generally by numeral 44 that fits into the normal water supply tubing or line to the toilet, indicated by numeral 46, and has the ability to control the amount of flow by a valve, indicated by numeral 48, associated with the conduit 42.

Thus, with reference to FIG. 2, it can be understood that the individual sits backward on the toilet seat, connects the conduit 42 to fitting 26 and then, by adjustively controlling the valve 48, provides a sufficient amount of water under pressure into the manifold to cause a flow to clean the ostomy 18 as seen in FIG. 1, and to provide a cleansing and irrigating action within the colostomy bag 10, with the residue dripping out at the bottom end into the toilet as shown generally by numeral 50.

Figure 3:
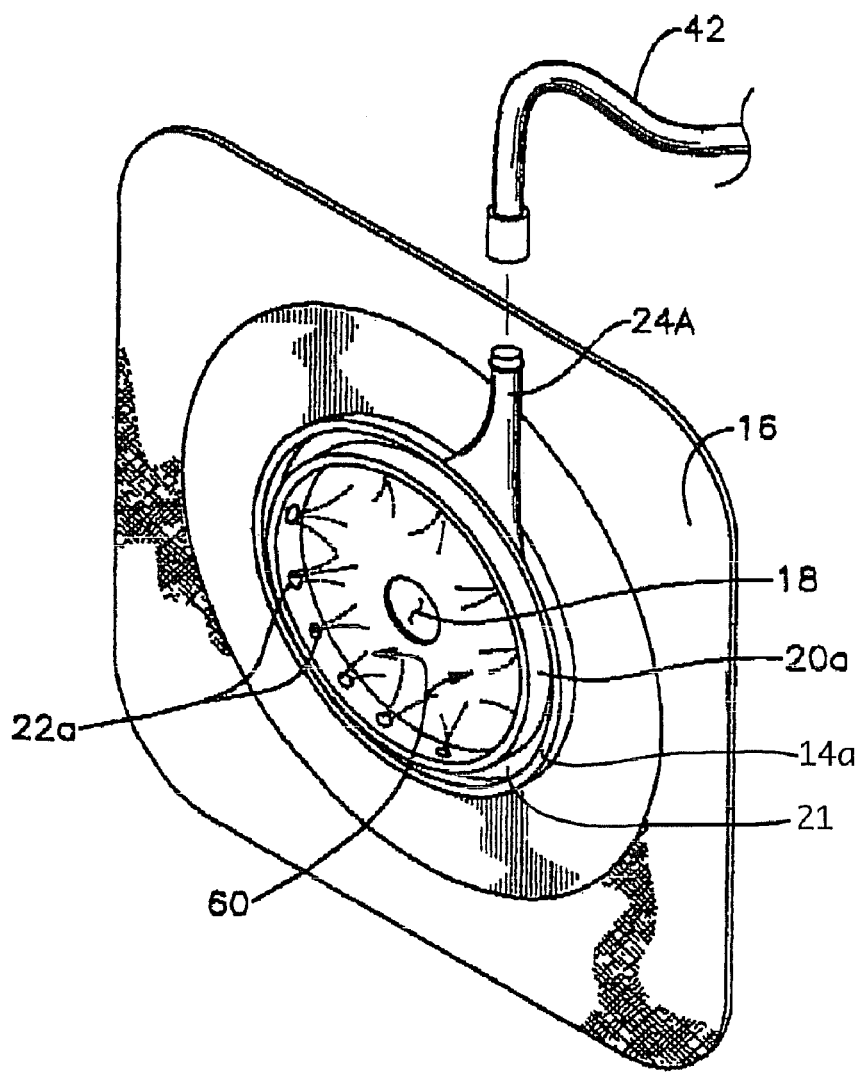
FIG. 3 is a perspective illustration of the manifold associated with the flanged ring and adhesive backed patch for attachment to a person, for engaging in a snapped fluid-tight relationship with the fitting on the colostomy bag, but wherein the manifold is associated with the flanged fitting or ring on the colostomy.

Referring now to FIG. 3 of the drawing, this shows the embodiment where the manifold, identified generally as numeral 20a, is associated with the ring 14A of the patch 16 that is attached to the skin of the person over the ostomy opening 18 so as to define a cavity 21 therebetween. In this instance, the ring 14A includes an access fitting 24A adaptively connected to the water line 42 so that regulated fluid under pressure provides the spray through orifices 22a illustrated generally by the numeral 60.

Figure 4:
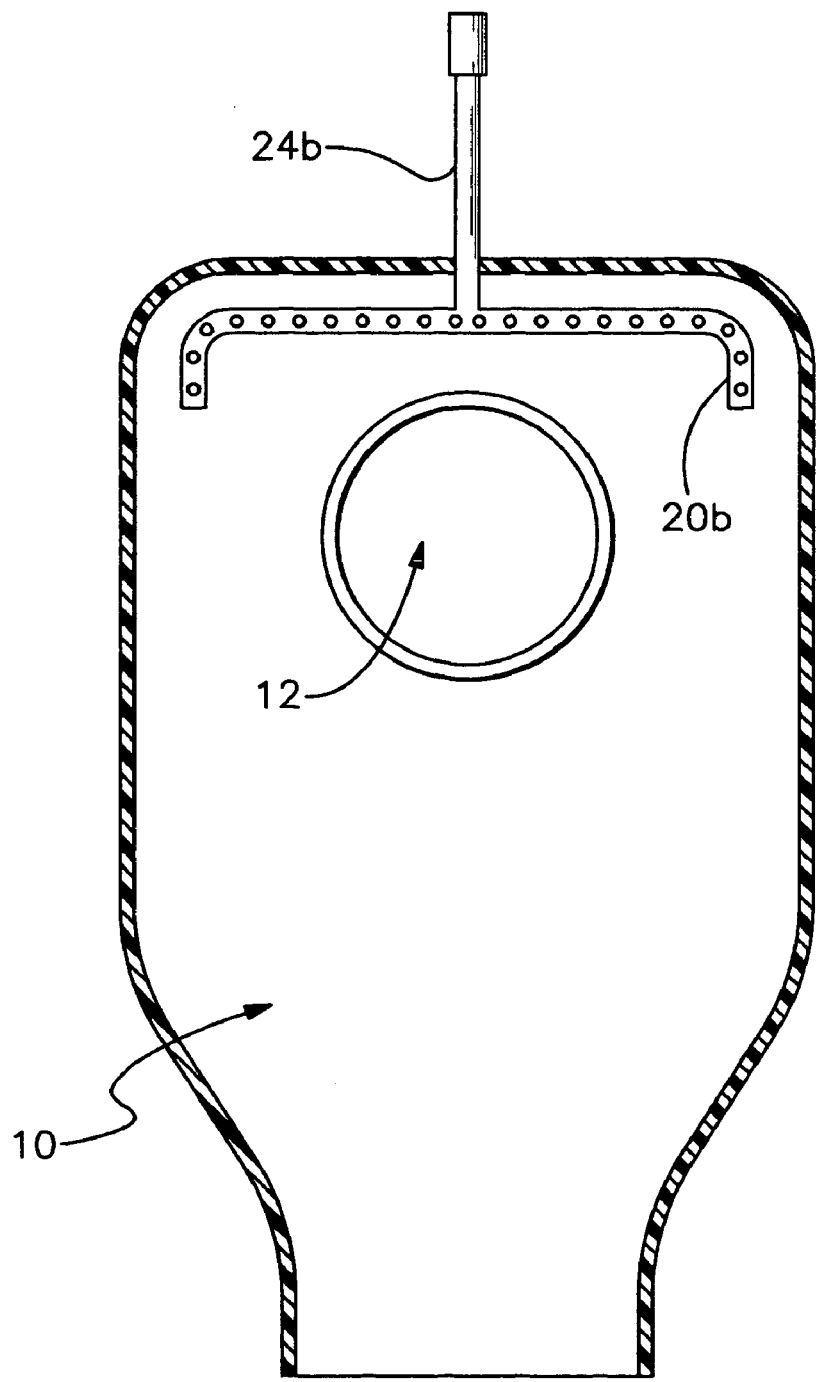
FIG. 4 illustrates a colostomy bag with the manifold positioned around the top of the bag itself and a water inlet being provided to the manifold around the top of the bag.

Referring now to FIG. 4, this shows a further embodiment of the invention where the manifold, indicated generally by numeral 20b, as can be seen is positioned above the inlet opening 12 in the colostomy bag 10. A similar water inlet 24b is utilized in this embodiment.

It should be understood that while FIG. 2 illustrates the fluid under pressure as coming from a water line 46 that normally provides water to the toilet itself, the invention contemplates that any suitable source of fluid under pressure will meet the objects of the invention. For example, a bottle of water with the ability to squeeze the bottle will provide fluid under pressure. Similarly, a small battery operated pump with a water source would provide fluid under pressure. It is believed that the invention will best be set up for a person to utilize in their own bathroom in their own home. However, there may be instances when they are traveling or not provided with a facility set up with the ability to hook the water hose to the adaptor 26 and feed the conduit 24 into the manifold, and thus any fluid supply system providing fluid under pressure will be suitable.

It is also to be understood that the spray holes 22 in the manifold are of no particular consequence except to provide a suitable, fairly fine, spray that will tend to both wash and clean and irrigate the residue inside the colostomy bag itself so as to facilitate cleaning in the shortest possible time. It has been found that this system can provide cleaning in just a few minutes and can be done several times a day very conveniently by virtue of the very simple application of water pressure through the manifold to clean the colostomy bag itself.

It is to be understood that the ease and the functioning of this invention is the fact that the manifold is positioned high in the colostomy bag, thus, with a large spray pattern clears the bag from the top down, and it has been found that it is desirable to have the manifold positioned no lower than the opening 12 in the colostomy bag for the stoma for attachment to the patch flange 14A. This then provides for good gravity flow of the water being used in the cleansing system, allowing it to flow down through the bag, picking up all residue and out the bottom end 30. It also should be understood that any colostomy bag that opens at the bottom will work with the invention.

It is to be understood that the scope of the invention is not to be limited by the descriptions and explanations set forth above, but that the invention encompasses any and all embodiments within the scope of the following claims.

We claim:

1. A colostomy bag system for collecting waste and cleansing while the bag is worn in an operable position on a wearer, said system comprising:

a colostomy bag having a top, an opening into an interior of the bag adjacent said top, a bottom end which is adapted to be repeatedly opened and sealed, and a first plastic ring formed with a first flange attached to the exterior of the bag surrounding the opening; and an attachment patch having an inlet therethrough and adhesive on a back thereof adapted to directly attach to the skin of the wearer proximate a stoma of the wearer with the inlet surrounding the stoma, said patch further including a circular manifold attached to a front of the patch surrounding the inlet, the manifold having a plurality of holes arranged in a circumferential relationship around a perimeter of the manifold with each of the plurality of holes in fluid communication with the inlet, a second plastic ring formed with a second flange, the second ring attached to the front of the patch surrounding the manifold, the second ring spaced from the manifold to define a circular cavity therebetween, and an access tube connected to the second ring for delivering fluid from an outside fluid source for passage first to the cavity, then through the plurality of holes of the manifold, the plurality of holes sized and oriented for spraying fluid radially toward a center of the manifold;

wherein, in the operable position, the first flange on the colostomy bag is adapted to snap together with the second flange on the patch for creating a fluid tight seal between the stoma and the interior of the bag; and wherein, when the colostomy bag is worn in said operable position, the bag collects digestive waste when the bottom end is sealed, and while still worn in the operable position, the colostomy bag is internally irrigated and cleaned and surfaces of the stoma exposed within the inlet are simultaneously externally cleaned when the bottom end is opened and fluid delivered from the outside fluid source.

2. The colostomy bag system of claim 1 further comprising:

a hose having a first end and a second end;
   the access tube being attached to the first end; and
   the second end adapted to be attached to the outside fluid source.

3. The colostomy bag system of claim 1, wherein the plurality of holes are adapted to direct fluid toward a center of the opening when in the operable position.

4. The colostomy bag system of claim 1, wherein the plurality of holes are adapted to direct fluid toward the exposed surfaces of the stoma of the wearer when in the operable position.

* * * * *